United States Patent [19]

Boettcher

[11] Patent Number: 5,101,053

[45] Date of Patent: Mar. 31, 1992

[54] RADIATION-SENSITIVE, ETHYLENICALLY UNSATURATED, COPOLYMERIZABLE SULFONIUM SALTS AND THEIR PREPARATION

[75] Inventor: Andreas Boettcher, Nussloch, Fed. Rep. of Germany

[73] Assignee: BASF Aktiengesellschaft, Ludwigshafen, Fed. Rep. of Germany

[21] Appl. No.: 462,558

[22] Filed: Jan. 9, 1990

[30] Foreign Application Priority Data

Jan. 25, 1989 [DE] Fed. Rep. of Germany ....... 3902114

[51] Int. Cl.$^5$ ................... C07F 9/68; C07D 333/08; G03C 1/00
[52] U.S. Cl. ................................. 556/64; 430/281; 430/287; 549/3; 549/6; 549/13; 549/80; 549/207; 549/218; 568/13; 568/23; 568/28; 568/42
[58] Field of Search ............... 556/64; 430/287, 281; 568/13, 23, 28, 42; 549/3, 6, 13, 80, 207, 218

[56] References Cited

U.S. PATENT DOCUMENTS

| | | | |
|---|---|---|---|
| 4,035,189 | 7/1977 | Hayashi et al. | 96/115 R |
| 4,136,102 | 1/1979 | Crivello | 260/440 |
| 4,151,175 | 4/1979 | Crivello et al. | 260/326.26 |
| 4,173,476 | 11/1979 | Smith et al. | 430/280 |
| 4,231,951 | 11/1980 | Smith et al. | 260/446 |
| 4,238,394 | 12/1980 | Crivello et al. | 260/326.26 |
| 4,339,567 | 7/1982 | Green et al. | 528/102 |
| 4,407,759 | 10/1983 | Crivello | 260/440 |
| 4,683,317 | 7/1987 | Crivello et al. | 556/64 |

FOREIGN PATENT DOCUMENTS

| | | |
|---|---|---|
| 0245662 | 11/1987 | European Pat. Off. |
| 3326036 | 1/1985 | Fed. Rep. of Germany |
| 3604581 | 8/1987 | Fed. Rep. of Germany |
| 1516511 | 7/1978 | United Kingdom |

OTHER PUBLICATIONS

Synthesis of Poly(p-hydroxy-alpha-methylstyrene)..., Marromolecules 1983, 16, 510-517, 1983.
Polymer 24, 995 (1983), Poly(p-tert-butoxycarbonyloxystyrene): ... Frechet et al., 995-1000, Aug. 1983.

Primary Examiner—Jose G. Dees
Assistant Examiner—Porfirio Nazario
Attorney, Agent, or Firm—Keil & Weinkauf

[57] ABSTRACT

Radiation sensitive sulfonium salts which contain (1) a sulfonium initiator portion, (2) a spacer portion, and (3) a reactive group portion. The spacer portion has the formula "-o-w- x-z-" wherein "w" is a single bond or one of —C(O)—, —C(O)O—, —C(O)S—, —C(O)NH— —C(O)N(alkyl)—, —C(S)—, —C(S)S—,—S(O)—, —S(O)(O)—, or —S(O)(O)O—; "X" is an unsubstituted or substituted alkylene radical; and "Z" is —O—, —NH—, —N(C,—C$_6$-alkyl)—, or —N(-phenyl)—. The reactive group portion is —CH=CH$_2$ or —C(O)—C(Y)=CH$_2$ wherein "Y" is H, C$_{1-6}$-alkyl, or phenyl. The sulfonium salts find use in curing monomers which can be subjected to cationic polymerization.

3 Claims, No Drawings

RADIATION-SENSITIVE, ETHYLENICALLY UNSATURATED, COPOLYMERIZABLE SULFONIUM SALTS AND THEIR PREPARATION

The present invention relates to novel radiation-sensitive, ethylenically unsaturated sulfonium salts and a process for their preparation.

Sulfonium salts are used for curing monomers which can be subjected to cationic polymerization. Previously, the said monomers, for example epoxides, were cured using acidic catalysts, as described in U.S. Pat. No. 3,842,019. For example, epoxides can be polymerized using boron trifluoride and its complexes, while styrene can be polymerized using aluminum trifluoride. Furthermore, 1,4-diazabicyclo[2.2.2]octane can be polymerized using benzenesulfonic acid. While the curing of such monomers with such catalysts gives successful results in many cases, acidic catalysts are often undesirable because catalysts of this type severely corrode various substrates, for example metals. In addition, many of these acidic catalysts do not have satisfactory stability as soon as they are mixed with the material to be polymerized. Furthermore, prior art catalysts, such as $BF_3 \cdot NH_2C_2H_5$, are sensitive to moisture.

According to U.S. Pat. No. 3,842,019, certain sulfonic acid salts which are exclusively thermally activated are used. However, these mixtures require curing temperatures of from 150° to 200° C. Such curable mixtures are unsuitable for the production of heat-sensitive electronic components. In particular cases, cationic curing of various compositions can be facilitated if a special photosensitive sulfonic acid salt, for example the corresponding silver salt, is used as the catalyst. However, the use of such metal sulfonate compositions is limited to special applications.

DE-A-25 18 652 describes curable compositions which contain a polymerizable epoxy resin and a radiation-sensitive onium salt, such as triphenyl sulfonium hexafluoroantimonate.

Onium salts are also used, inter alia, in microlithography for photochemical solubility differentiation. The special onium salts described in DE-A-27 54 853 eliminate, on exposure, a strong, nonnucleophilic acid, which serves for solubility differentiation of photopolymers (cf. for example Polym. Eng. Sci. 23 (1983), 953), in that an acid-labile protective group, for example the tert-butoxycarbonyloxy group (cf. Polymer 24 (1983), 995; Macromolecules 16 (1983), 510 and Polym. Eng. Sci. 23 (1983), 1022) is eliminated by the acid produced.

Moreover, DE-A-37 21 740 describes sulfonium salts which contain one or more groups which can be eliminated by an acid.

The onium salts are added to the monomer/polymer mixtures (cf. Chim. Nuov. 4 (1986), 343). In general, however, such procedures are not entirely satisfactory since problems with the compatibility, the solubility, the uniformity, the distribution, the volatility, the odor, the toxicity, the exudation and the migration of the additive occur after mixing with the polymer, the said problems frequently leading to an undesirable, premature and nonuniform reaction In the actual exposure process, low reactivity is then observed owing to a reduced effective initiator concentration, and a number of troublesome side reactions are observed after exposure.

Sulfonium salts are frequently used as initiators for the production of semiconductor photoresists. During application of the oligomer mixtures, dissolved in an organic solvent, to a substrate an increase in the concentration of the polar sulfonium salt in the lower regions of the polymer layer, in which regions the solvent remains longest, is frequently observed (cf. Macromolecules 16 (1983), 510) during evaporation of the solvent. This results in a photopolymer layer having an initiator concentration gradient which leads to poor, nonuniform curing results.

From the chemistry of other photoinitiator classes, it is known that some of the stated problems can be solved if the radiation-sensitive initiator is copolymerized with monomers by a conventional process, i.e. is incorporated in a polymer chain. The photosensitive photoinitiator is attached to the base polymer by an anchor group, i.e. a spacer. The spacer also serves to reduce the influence of the base polymer chain on the photochemical behavior of the initiator.

Copolymerizable initiators therefore have in principle the following structure:

Scheme I

A number of polymer-bound sulfonium salts, for example

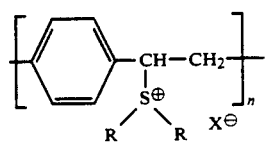

(cf. Polymer 27 (1986), 1709),

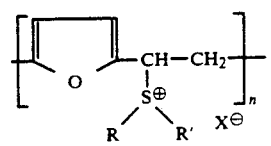

(cf. EP-A-246 931) and

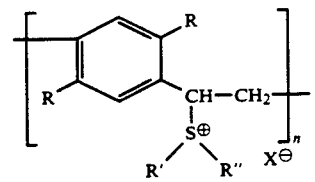

(cf. EP-A-246 931, Polym. Commun. 26 (1985), 362) where R, R' and R" are each alkyl, X is halogen and n is ≧5, have already been described.

Sulfonium salts having ethylenically unsaturated, reactive groups are used as latent thermal catalysts

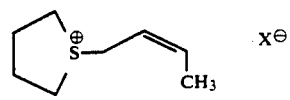

(cf. Makromol. Chem. Rapid Commun. 6 (1985), 137) or as copolymerizable monomers:

[Structure: styrene with CH₂-S⁺ (cyclic sulfonium), X⁻ counterion]

(cf. J. Polym. Sci., Part C, Polym. Lett. 26 (1988), 77).

All polymer-bound sulfonium salts known to date are less toxic and form a smaller amount of volatile by-products during photolysis than the corresponding monomeric onium salts.

However, the abovementioned sulfonium salts are photochemically less reactive since the spacer is very short and in some cases completely absent. The onium group thus has little conformative mobility.

It is an object of the present invention to provide novel copolymerizable sulfonium salts of the types

| $\backslash\overset{\oplus}{S}\sim$ | —O—W—X—Z— | $\underset{\underset{O}{\|}}{C}-\underset{Y}{\overset{\|}{C}}=CH_2$ |
|---|---|---|
| Initiator | Spacer | Reactive group |

| $\backslash\overset{\oplus}{S}\sim$ | —O—W—X—Z— | CH=CH₂ |
|---|---|---|
| Initiator | Spacer | Reactive group | which do not have the abovementioned disadvantages and are particularly stable to migration.

We have found that this object is achieved by radiation-sensitive, ethylenically unsaturated, copolymerizable, organic compounds of the general formula (I)

$$[(R)_a(R^1)_b(R^2)_c S^{\oplus}] A^{\ominus} \quad (I)$$

where
R is an unsubstituted or substituted monovalent aromatic organic radical,
$R^1$ is an unsubstituted or substituted monovalent organic aliphatic radical from the group consisting of the alkyl, cycloalkyl and substituted alkyl radicals,
$R^2$ is an unsubstituted or substituted divalent or trivalent aliphatic or aromatic organic radical which forms a heterocylic or fused ring structure,
a is an integer from 0 up to and including 3,
b is an integer from 0 up to and including 2,
c is the integer 0 or 1,
the sum a+b+c being 3,
e is an anion of an acid and
$A^{\ominus}$ is an anion of an acid and
at least one of the radicals R to $R^2$ contains one of the radical —O—W—X—Z—C—C=CH₂ or
　　　　　　‖ |
　　　　　　O Y

—O—W—X—Z—CH=CH₂ where
W is a single bond or one of the groups $$-\underset{\|}{\overset{O}{C}}-, -\underset{\|}{\overset{O}{C}}-O-, -\underset{\|}{\overset{O}{C}}-S-, -\underset{\|}{\overset{S}{C}}-,$$

$$-\underset{\|}{\overset{S}{C}}-S-, -\underset{\|}{\overset{O}{S}}-, -\underset{O}{\overset{O}{\underset{\|}{\overset{\|}{S}}}}-, -\underset{O}{\overset{O}{\underset{\|}{\overset{\|}{S}}}}-O-,$$

$$\underset{/}{\overset{O}{\backslash\overset{\|}{P}}}-, \underset{/}{\overset{S}{\backslash\overset{\|}{P}}}-, -\underset{\|}{\overset{O}{C}}-NH-, -\underset{\|}{\overset{O}{C}}-N(Alkyl)-$$

where alkyl is, for example, methyl, ethyl, n-propyl, isopropyl or n-butyl, and
X is a divalent, unsubstituted or substituted alkylene radical —(CH₂)ₘ—, a radical $$\left( -\underset{R''}{\overset{R'}{\underset{|}{\overset{|}{C}}}}- \right)_m$$

where m is from 1 to 10 and R' and R" are identical or different and are each aryl, e.g. phenyl, $C_1$-$C_4$-alkyl, H, COOH, COOCH₃ or COOC₂H₅, or X is a perfluorinated alkylene radical —(CF₂)ₘ—, where m is from 1 to 10, preferably a perfluoroethylene radical, for example a tetrafluoroethylene radical, an oxaalkylene radical of the type —(CH₂)ₙ—O—(CH₂)ₚ—, where n and p are each from 1 to 5, preferably 2, i.e. —C₂H₄—O—C₂H₄—, a perfluorinated oxaalkylene radical of the type —(CF₂)ₙ—O—(CF₂)ₚ—, where n and p are each from 1 to 5, or a polyoxaalkylene radical which may be perfluorinated and has from 2 to 20 oxygen atoms which are bonded to one another by at least one —CH₂—, —CF₂— or —CH₂—CH(CH₃)— group, or an alkylene radical of the type —(CH₂)ₘ—O—CO—O—(CH₂)ₙ—, —(CH₂)ₙ—O—CO—NH—(CH₂)ₘ—, —(CH₂)ₙ—NH—CO—O—(CH₂)ₘ—, —(CH₂)ₘ—CO—O—(CH₂)ₙ—or —(CH₂)ₘ—O—CO—(CH₂)ₙ—, where m and n are each from 1 to 10, a phenylene radical which is unsubstituted or substituted by alkyl of 1 to 4 carbon atoms, e.g. methyl, ethyl, n-propyl, isopropyl, OH, OCH₃, OC₂H₅, SH, SCH₃, SC₂H₅, Cl, F, N(alkyl)₂ or N(CH₃)C₆H₅ in the o-, m- and/or p-position, or a cycloalkylene radical of 5 to 10 carbon atoms, e.g. cyclohexylene or cyclooctylene, or a (bis)methylenecycloalkylene radical of 6 to 12 carbon atoms,
Y is H, alkyl of 1 to 6 carbon atoms or phenyl and Z is O or NY.

Examples of R in the general formula (I) are unsubstituted or substituted $C_6$-$C_{13}$ aromatic hydrocarbon radicals, such as phenyl, tolyl, 4-(phenylthio)phenyl, naphthyl, anthryl, etc., and such aromatic hydrocarbon radicals substituted by 1 to 4 monovalent radicals, where the substituents may be $C_1$-$C_8$-alkoxy, $C_1$-$C_8$-alkyl, nitro, chlorine, hydroxyl, etc.; R may furthermore be arylalkyl, such as benzyl, phenacyl or an aromatic heterocyclic radical, such as pyridyl, furfuryl, etc.

$R^1$ includes $C_1$-$C_8$-alkyl, such as methyl, ethyl, etc., substituted alkyl, such as —C₂H₄OCH₃, —CH₂COOC₂H₅, —CH₂COCH₃, etc.

The radicals R² include structures such as

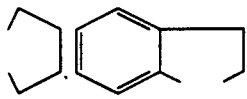

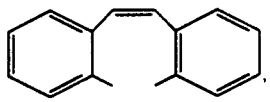

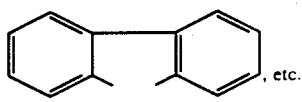, etc.

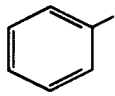

The anions A⊖ in formula (I) are, for example, BF₄⊖, PF₆⊖, AsF₆⊖, SbF₆⊖, ClO₄⊖, CF₃SO₃⊖, AlCl₄⊖, BCl₄⊖, Br⊖, Cl⊖, HSO₄⊖, CH₃CO₂⊖, NO3⊖, etc. and (MSO₃)⊖, where M is selected from the group consisting of the aromatic C₁-C₁₃-hydrocarbon radicals, C₁-C₈-alkyl radicals, their halogenated derivatives and fluorine.

Surprisingly, the novel compounds have particularly high photochemical reactivity both in the short-wavelength UV range of 250-350 nm and in the longer wavelength range of 330-430 μm, depending on their substitution pattern.

It is a further object of the present invention to provide a process for the preparation of novel, radiation-sensitive, copolymerizable sulfonium salts having at least one acrylate or vinyl ether terminal group.

We have found that this object is achieved by reacting hydroxyl-containing sulfonium salts with isocyanates or chloroformates or their thermally stable intermediates in the presence or absence of a catalyst.

We have found, surprisingly, that the novel sulfonium salts are obtainable readily and in very good yield. This is particularly unexpected in view of the reactivity and bifunctionality of the (meth)acrylate, vinyl ether and isocyanate component, since many different reaction products are possible.

The present invention furthermore relates to a process for the preparation of compounds of the general formula (I), wherein a compound of the formula (II), (III) or (IV)

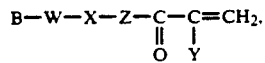
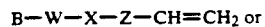
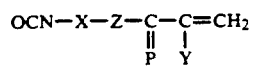

where
W, X, Y and Z have the abovementioned meanings and
B is one of the groups tosylate, alkoxy of 1 to 5 carbon atoms, halogen, eg Cl or Br, chlorocarbonyl, imidazolyl, pyrazolyl or an ammonium, pyridinium, phosphonium or sulfonium cation, preferably, for example, a 2-(acryloyloxyethyl) or 2-(metha-cryloyloxyethyl)chlorocarbonate, a 2-(methacryloyloxyethyl)chloroglyoxylate or a (2-(meth)acryloyloxyethyl)methyl carbonate, is reacted with a compound of the general formula (V)

$$[(R)_a(R^1)_b(R^2)_c S^{\oplus}]A^{\ominus} \quad (V)$$

where
R is an unsubstituted or substituted monovalent aromatic organic radical,
R¹ is an unsubstituted or substituted monovalent organic aliphatic radical from the group consisting of the alkyl, cycloalkyl and substituted alkyl radicals,
R² is an unsubstituted or substituted divalent or trivalent aliphatic or aromatic organic radical which forms a heterocylic or fused ring structure,
a is an integer from 0 up to and including 3,
b is an integer from 0 up to and including 2,
c is the integer 0 or 1,
the sum a+b+c being 3, and
A⊖ is an anion of an acid and
at least one of the radicals R to R² contains a hydroxyl group, for example

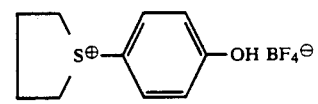

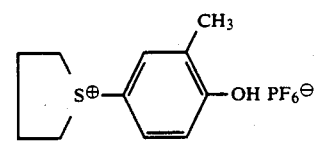

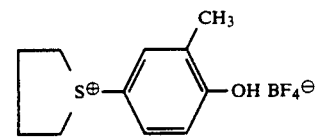

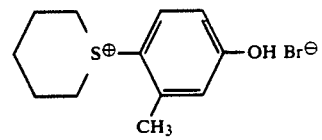

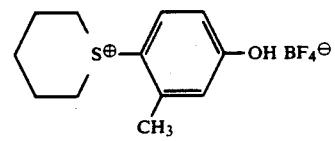

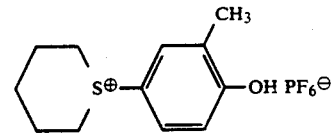

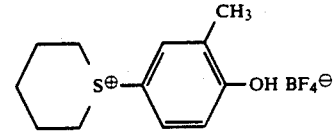

-continued
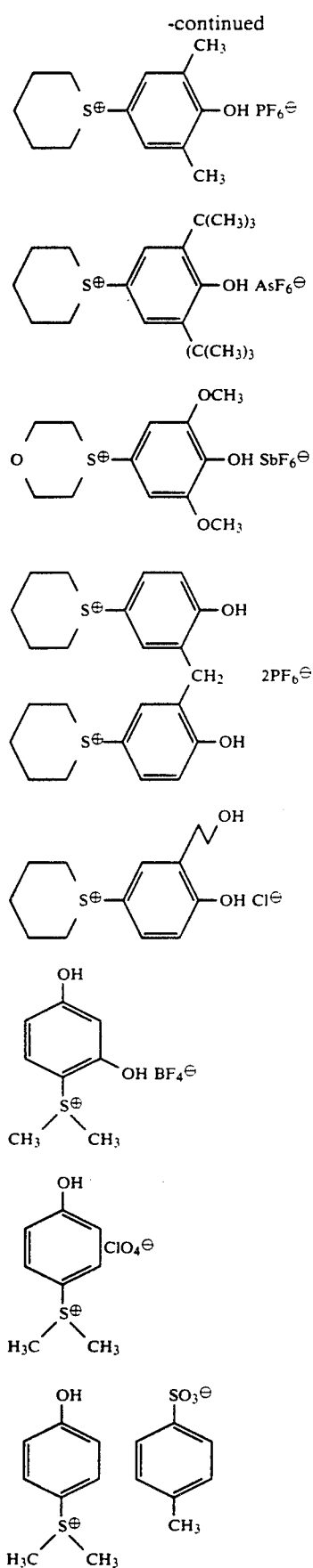
-continued
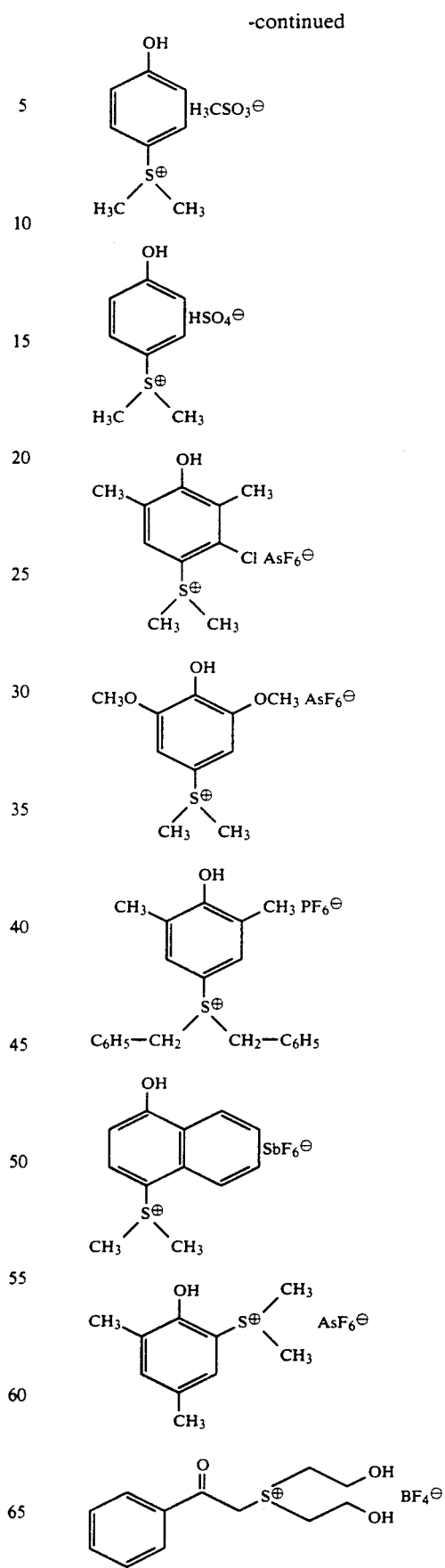

-continued

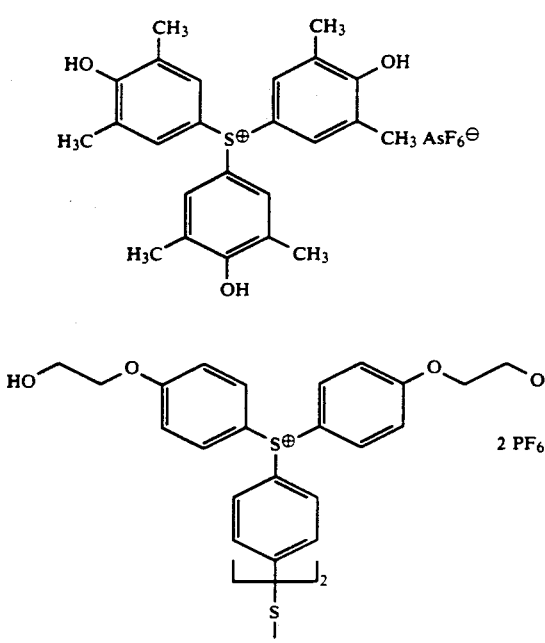

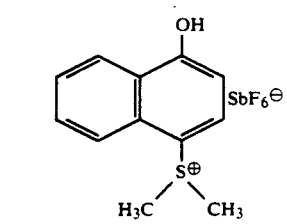

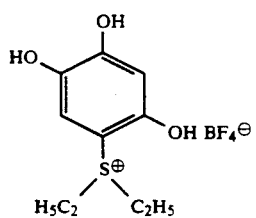

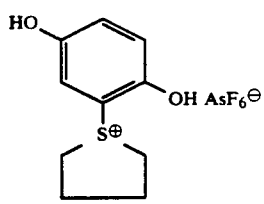

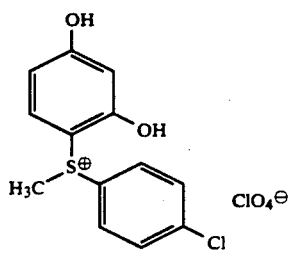

-continued

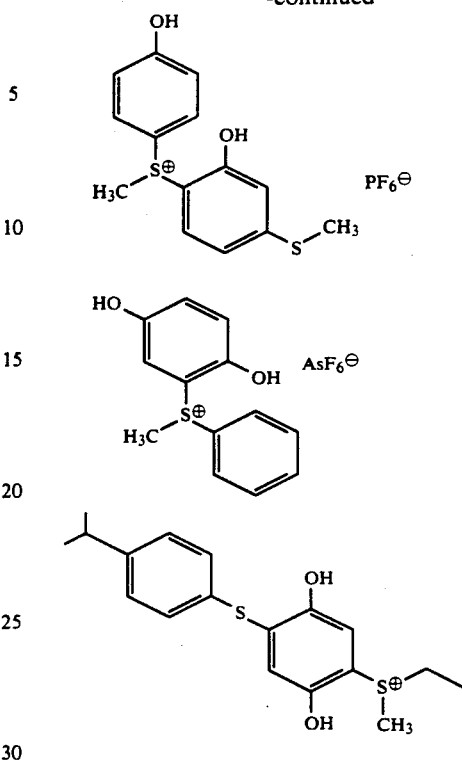

in an equimolar ratio (if necessary with up to 10-30% excess) or, depending on the number of hydroxyl groups in the radicals R to $R^2$, in two or three times the equimolar ratio, in the presence or absence of an inert solvent or solvent mixture and of a basic catalyst, at from 0° to 100° C., preferably from 10° to 60° C.

Some chloroformates used in the reaction and the isocyanates react readily with nucleophiles, including water. It is therefore important to carry out the reaction in the absence of moisture by using dry and/or weakly nucleophilic or nonnucleophilic solvents, eg. acetonitrile, dichloromethane, dichloroethane, tetrahydrofuran, toluene, xylene, chlorobenzene, ethyl acetate, chloroform, etc., and if necessary to establish an inert gas atmosphere, for example nitrogen, argon or carbon dioxide.

The syntheses of the hydroxysulfonium salts required as starting materials are known. The following references may be stated as examples:

J. Am. Chem. Soc. 80 (1958), 3425;

J. Polym. Sci. Polym. Chem. Ed. 18 (1980), 1021;

Polym. Prep. Am. Chem. Soc. Div. Polym. Chem. 25 (1984), 262;

Polym. J. 17 (1985), 73; U.S. Pat. Nos. 4,336,363, 4,417,061, 4,650,734 and 4,684,671; European Patent 245,662; Japanese Patent 61,212,555; German Laid-Open Application DOS 1,951,803; German Patent 2,541,709, etc., and the literature cited herein.

The ω-(meth)acryloyloxyalkyl chloroformates can be prepared conveniently and in good yields by processes known in the literature, as described in, for example, Eur. Polym. 14 (1978), 205; J. Polym. Sci. Polym. Symp. 66 (1979), 41 and Bull. Soc. Chim. Belg. 93 (1984), 159.

Examples of compounds of this type are:

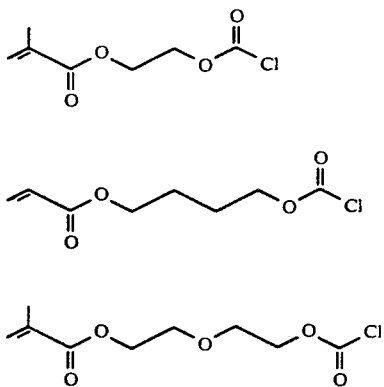

Other methods for the preparation of the chloroformates, which are particularly suitable for laboratory syntheses, are arrived at through the choice of the phosgenating agents. Examples of alternative phosgenating agents are trichloromethyl- chloroformate (diphosgene), J. Prakt. Chem. 126 (1930), 210, ibid 128 (1930), 233, Chem. Abstr. 95, 81766, J. Org. Chem. 50 (1985), 715, J. Org. Chem. 41 (1976), 2070, Angew. Chem. 89 (1977), 267, crystalline triphosgene, Angew. Chem. 99 (1987), 922, N,N'-carbonyldiimidazole or N,N'-carbonyldi-s-triazole (Fieser 1 (1967), 116).

For example, the following can be prepared with the aid of these reagents:

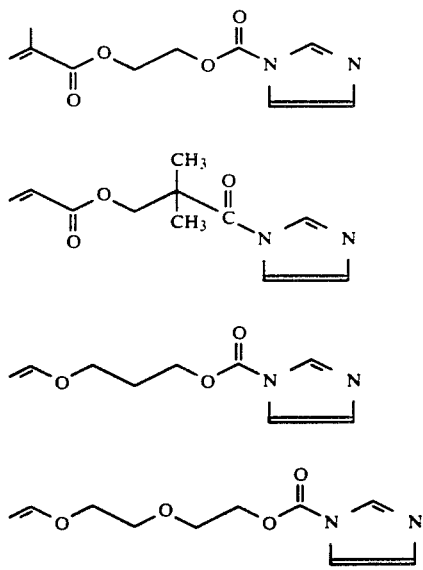

Merck Kontakte 1981 (1), 1–18 gives information about the use of further special alternative processes for phosgenation, for example reaction with chlorocarbonates.

The reaction of p-hydroxyphenylphosphonium salts with activated acyl chlorides is described in EP-A-245 662. The following compounds

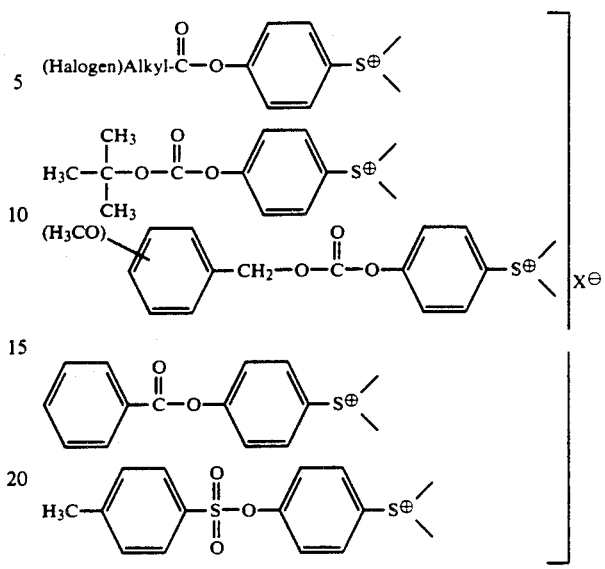

are prepared from the corresponding acid chlorides or chloroformates. The sulfonium salts are very reactive; they are used in the form of activated esters in peptide synthesis. It is surprising that the chloroformates of the hydroxyalkyl (meth)acrylates are stable to nucleophiles and in some cases can even be recrystallized from isopropanol. These properties make them particularly interesting for use in polymers having nucleophilic groups.

The ω-isocyanatoalkyl (meth)acrylates can be synthesized in good yield by the processes described in EP-A-083 764 and DE-A-35 23 692. The following isocyanates are examples:

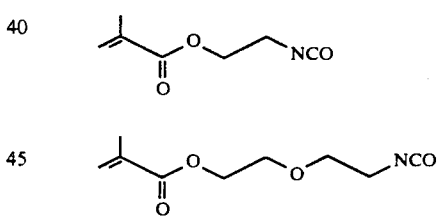

Other isocyanates are obtained in a conventional manner, for example by the process of U.S. Pat. No. 2,718,516, in which an alkanolamine is reacted with ethyl chloroformate, the resulting hydroxyalkyl ethyl carbonate is acylated with methacryloyl chloride and the resulting urethane is cleaved in the presence of a basic catalyst with heating, or by the process of U.S. Pat. No. 2,821,544, in which methacryloyl chloride is also reacted with an alkanolamine hydrochloride and the resulting ω-aminoalkyl methacrylate is then reacted with phosgene. Examples of suitable alkanolamine hydrochlorides are:

-continued

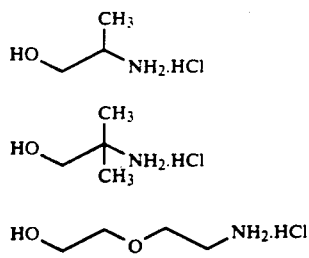

The literature contains similar examples for the reaction of the hydroxy(aryl)sulfonium salts with the isocyanates to give the corresponding aryl carbamates.

The synthesis of aryl carbamates without copolymerizable terminal groups is known C. Ferri, Reaktionen der organischen Synthese, G. Thieme Verlag, Stuttgart, 1978, gives an overview.

The most important preparation process is the reaction of aromatic alcohols with isocyanates (cf. Houben-Weyl VIII, page 141; O. S. Petersen, Liebigs Ann. Chem. 562 (1947), 205; J. Burkus, J. Org. Chem. 26 (1961), 779; I. T. Kay and N. Punja, J. Chem. Soc. [C] 1968, 3011; L. Capuano and R. Zander, Chem. Ber. 104 (1971), 2212). The carbamates are formed in good to very good yields when an alcohol and an isocyanate are reacted with one another in a molar ratio of 1:1 without a solvent or in excess alcohol as the solvent Where the alcohol or the phenol is in the form of a solid, an aprotic solvent, eg. dichloromethane, dichloroethane, acetonitrile, toluene, etc., is used.

In extrapolating this preparation process to ω-isocyanatoalkyl (meth)acrylates of the general formula (IV), where X is an alkylene radical which may be perfluorinated, an oxaalkylene radical or a polyoxaalkylene radical, each of 2 to 12 carbon atoms, and Y is H— or CH$_3$—, we have found, surprisingly, that the desired carbamoyl-substituted sulfonium salts having (meth)acrylate groups are formed in a high, virtually quantitative yield. This is surprising in that acrylates and methacrylates can readily undergo many side reactions (crosslinking, polymerization).

The good to excellent yields in the presence of sulfonium groups are also surprising.

Regarding the preparation process, the following may be stated specifically:

As a rule, a solution or suspension of the hydroxy compound in an inert solvent, which may also be omitted if the compound is liquid at the reaction temperature, is initially taken at from 0° to 100° C., preferably from 10° to 60° C., in the presence of a basic, weakly nucleophilic or nonnucleophilic amine, preferably triethylamine, 4-dimethylaminopyridine, imidazole, 1,4-diazabicyclo[2.2.2]octane, 1,5-diazabicyclo[4.3.0]non-5-ene, 1,8-diazabicyclo[5.4.0]undec-7-ene, polyvinylpyridine, N,N-dimethylpropyleneurea, N,N'-dimethylethyleneurea, etc. Then, for example, the chloroformyl compound, which may be dissolved in an inert solvent, eg. dichloromethane, dichloroethane, acetonitrile, toluene, chlorobenzene, xylene, etc., is added dropwise with stirring in the abovementioned temperature range. This procedure is particularly suitable for relatively large batches.

After stirring has been continued for from 1 to 48, preferably from 1 to 20, hours at from 10° to 30° C., filtration, washing and drying are carried out by standard methods and the product is isolated after recrystallization, distillation or extraction.

The present invention also relates to cationically curable mixtures which contain a novel copolymerizable sulfonium salt as the catalyst, can be cured by heating or exposure to actinic light and are suitable for the production of moldings, coatings, relief images and resist patterns.

Cationically curable mixtures, such as epoxy resins, are usually cured using carboxylic acids or anhydrides thereof or by the addition of other Lewis acids. Because of the high reactivity, the two components must be handled separately and processed rapidly after mixing. There has been no lack of attempts to develop single-component systems which have a longer shelf life and can be cured either by heating or by exposure to light of a suitable wavelength. Many photoinitiators have been described as catalysts for light-induced curing, including in particular the diazonium salts of U.S. Pat. Nos. 3,205,157 and 3,708,296 and the onium salts of the elements of main groups V (cf. DE-A-2 518 656), VI (cf. DE-A-2 518 652 and DE-A-904 626) and VII (cf. DE-A-2 518 639) of the Periodic Table of the Elements and the sulfoxonium salts stated in EP-A-22 081, EP-A-35 969 and EP-A-44 274. However, these compounds have unsatisfactory properties On exposure, diazonium salts release nitrogen, which may lead to bubble formation in the moldings and coatings produced using diazonium salts. The iodonium salts of DE-A-2 518 639 are toxic; like the sulfonium salts of DE-A-2 518 652 and DE-A-2 904 626, they furthermore absorb only weakly in the wavelength range of 300–400 nm, so that in general a sensitizer has to be added to the photocurable mixture. Furthermore, some of the sulfonium salts according to DE-A-2 518 652 and DE-A-2 904 626 release foul-smelling low molecular weight sulfur compounds on exposure to actinic light. The sulfoxonium salts of EP-A-22 081, EP-A-35 969 and EP-A-44 274 can only be obtained by an involved procedure using expensive organometallic reagents, which makes them more difficult to produce in industrial amounts.

DE-A 2 853 886 describes, as a catalyst for heat-curable systems, a combination of an iodonium salt and a Cu$^I$ salt, which however can only be used with considerable safety measures, owing to the highly toxic iodonium salt. Another catalyst combination is the mixture of pyrylium salts and metal chelates, described in DE-A 3 135 636; however, the shelf life of the mixtures prepared with the aid of this initiator combination is unsatisfactory It is a further object of the present invention to provide cationically curable mixtures which contain a cationic curing catalyst, have a long shelf life, are easy to handle, can be processed and are non-toxic and which give moldings having a good surface and solvent resistance after curing.

The novel curable compositions contain, for example,
a) a compound or a mixture of compounds which can be converted into a higher molecular weight material under the influence of a cationic catalyst and
b) preferably 0.1–15% by weight, based on the amount of the compounds a), of the novel sulfonium salts described above.

The compounds a) may be, for example, oxetanes, thiiranes or tetrahydrofuran. Compound a) is preferably a 1,2-epoxide, an olefinically unsaturated compound, an aminoplast or a phenoplast, provided that they are cationically curable or polymerizable Examples of suitable 1,2-epoxides are epichlorohydrin, propylene oxide and glycidyl ethers of a monohydric alcohol or of a phenol, such as n-butyl glycidyl ether or phenyl glycidyl ether, and glycidyl esters, such as glycidyl acrylate or glycidyl methacrylate. Component a) is preferably an epoxy resin, in particular one which contains at least one group of the formula (VI)

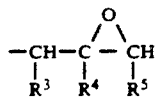  (VI)

which is bonded directly to an oxygen atom and in which either $R^3$ and $R^5$ are each hydrogen, in which case $R^4$ is hydrogen or methyl, or $R^3$ and $R^5$ together form —$CH_2CH_2$—, in which case $R^4$ is hydrogen. Examples of such resins are polyglycidyl and poly($\beta$-methylglycidyl) esters, which can be obtained by reacting a compound containing two or more carboxylic acid groups with epichlorohydrin, glycerol dichlorohydrin or $\beta$-methylepichlorohydrin in the presence of an alkali. Such polyglycidyl esters may be derived from aliphatic polycarboxylic acids, such as succinic acid, glutaric acid, adipic acid, pimelic acid, suberic acid, azelaic acid, sebacic acid or dimerized or trimerized linoleic acids, cycloaliphatic polycarboxylic acids, such as tetrahydrophthalic acid, 4-methyltetrahydrophthalic acid, hexahydrophthalic acid and 4-methylhexahydrophthalic acid, and from aromatic polycarboxylic acids, such as phthalic acid, isophthalic acid and terephthalic acid. Other suitable polyglycidyl esters are obtainable by polymerization of the glycidyl esters of olefinically unsaturated acids, in particular of glycidyl acrylate and glycidyl methacrylate.

Polyglycidyl and poly($\beta$-methylglycidyl) ethers, such as those which are obtainable by reacting a compound containing at least two free alcoholic and/or phenolic hydroxyl groups in the molecule with the corresponding epichlorohydrin under alkaline conditions, or in the presence of an acidic catalyst with subsequent treatment with an alkali, are also suitable. Examples of alcohols and phenols for such a reaction are ethylene glycol, propanediol, diethylene glycol, poly(oxyethylene) glycols, poly(oxypropylene) glycols, poly(oxytetramethylene) glycols, glycerol, 1,1,1-trimethylolpropane, pentaerythritol, sorbitol, bis-(4-hydroxycyclohexyl)-methane, 2,2-bis-(4-hydroxycyclohexyl)-propane, N,N-bis-(2-hydroxyethyl)aniline, p,p'-bis-(2-hydroxyethylamino)diphenylmethane, bis-(4-hydroxyphenyl)propane and novolaks, such as can be prepared by reacting aldehydes, such as formaldehyde or acetaldehyde, with phenols.

Examples of epoxy resins with groups of the formula VI, where $R^3$ and $R^5$ together form a —$CH_2CH_2$— group, are bis-(2,3-epoxycyclopentyl) ether or 2,3-epoxycyclopentyl glycidyl ether.

Epoxy resins in which some or all of the epoxide groups are in the middle, such as vinylcyclohexene dioxide and dicyclopentadiene dioxide, and epoxidized polybutadienes or epoxidized butadiene copolymers with vinyl monomers can also be used. It is of course also possible to use epoxy resin mixtures.

Particularly preferably used epoxy resins are the diglycidyl ethers of dihydric phenols and of dihydric aliphatic alcohols.

If desired, the epoxy resin may also be subjected in a known manner to cocuring with a polyhydric alcohol, in particular one having a molecular weight of more than 1,000. Examples of suitable alcohols for this purpose are poly(oxyethylene) glycols, polyvinyl alcohols, hydroxypropylcellulose and partial esters of cellulose.

Olefinically unsaturated monomers a) which can be subjected to cationic polymerization with the novel sulfonium salts are, for example, styrene, $\alpha$-methylstyrene, divinylbenzene, vinylcyclohexane, 4-vinylcyclohex-1-ene, N-vinylcarbazole, isoprene, butadiene and preferably vinyl ethers, such as methyl vinyl ether, isobutyl vinyl ether, 1,1,1-trimethylolpropane trivinyl ether, glycerol trivinyl ether, the vinyl ethers of ethylene glycol and polyethylene glycols and cyclic vinyl ethers.

The aminoplasts as preferred components a) contain, per molecule, at least two methylol groups which are bonded to an amide or thioamide nitrogen atom or atoms and may also be etherified or esterified. Examples of such aminoplasts are the N-hydroxymethyl, N-methoxymethyl, N-butoxymethyl and N-acetoxymethyl derivatives of urea, thiourea or cyclic ureas, of carbamates and dicarbamates of aliphatic monohydric and dihydric alcohols and of melamine, such as partially etherified hexamethylolmelamine, and of other polyamino-1,3-triazines. Preferred aminoplasts are the condensates of urea, of hydantoin or of melamine with formaldehyde, for example a condensate of urea with 1.8 moles of formaldehyde, and partially or completely etherified products of such condensates with an aliphatic monohydric alcohol of 1 to 4 carbon atoms, such as hexamethoxymethylmelamine.

Preferred phenoplasts are the known resols prepared from a monohydric or polyhydric phenol and an aldehyde, such as formaldehyde Suitable additives, such as diluents, reinforcing agents, fillers, dyes, pigments, processing assistants and other conventional additives, the type and amount of which are familiar to the skilled worker, may be added to the novel curable mixtures.

The curable resin compositions prepared with the aid of the novel sulfonium salts may furthermore contain, as an additional component, for accelerating the curing, an oxidizing agent from the class consisting of the quinones and of the organic peroxides. Suitable compounds are, for example, ketone peroxides, peroxy acids, aldehyde peroxides, hydroperoxides, especially alkyl peroxides, diacyl peroxides and alkyl esters of per acids, for example butyl peroxypivalate, benzoyl peroxide, di-tertbutyl peroxide, tert-butyl hydroperoxide, methyl ethyl ketone peroxide and m-chloroperbenzoic acid. Examples of suitable quinones are the benzoquinones which are completely or partially substituted by chlorine or cyano, such as chloranil or 2,3-dichloro-5,6-dicyanobenzoquinone.

The novel curable mixtures contain in general from 0.1 to 15, preferably from 0.5 to 10, % by weight of the novel sulfonium salts and, if required, 0.01-10, preferably 0.05-2, % by weight of the abovementioned oxidizing agent, the percentages in each case being based on the total amount of the curable compounds a).

The novel mixtures can be cured by heating or by exposure to actinic light of wavelength 200–600 nm, the optimum curing method depending on the components used in the mixtures and on the intended use of the latter. The novel compositions preferably also contain a sensitizer. We have found that incorporation of suitable sensitizers further increases the curing rate, permitting the use of even shorter exposure times and/or less powerful radiation sources. Furthermore, the sensitivity to visible light is increased. Suitable sensitizers are acetophenone derivatives, such as benzil dimethyl ketal or benzoin ethers, benzophenone or its derivatives and thioxanthone derivatives, such as 2-methyl- or 2-isopropylthioxanthone. Other suitable sensitizers are polycyclic aromatics, such as anthracene, phenanthrene, rubrene, perylene and pyrene 0.1-2% by weight, based on the total amount of components a), of sensitizers are preferably employed.

Suitable actinic radiation sources for photocuring at wavelengths of 200-600 nm are the known ones, such as carbon arc lamps, mercury vapor lamps, fluorescent tubes emitting ultraviolet light, argon and xenon glow lamps and photographic floodlights. The time required for exposure depends on, inter alia, the polymerizable material used and the type of light source and its distance from the exposed material and can readily be determined by the skilled worker in a preliminary test.

If the curable compositions is to be heat-cured, it is brought into a suitable form, for example cast as a thin film. For curing, the resin is heated to 80°-160° C., preferably 100°-150° C.

The novel compositions can be used, for example, for surface coatings and can be cured by exposure or heating after application to a substrate, such as steel, aluminum, copper, cadmium, zinc, paper or wood. If exposure is effected through a mask, the unexposed parts of the layer can be removed by washing out. The novel mixtures are particularly suitable for the production of printing plates and printed circuits, and the known methods for the production of printing plates and printed circuits from photopolymerizable compositions can be used.

The novel mixtures can also be used as adhesives, for the production of fiber-reinforced composite materials, including sheet molding compounds, for the production of cements and filling compounds or for dip coating.

A novel mixture containing, for example, an epoxy resin or phenoplast and an amount of the novel sulfonium salt which is effective during exposure of the composition to actinic radiation for polymerization of this epoxy resin or phenoplast may also contain an effective amount of a latent heat-curing agent for the epoxy resin or phenoplast, such as polycarboxylic anhydrides, complexes of amines, in particular primary or tertiary aliphatic amines, with boron trifluoride or boron trichloride. Latent crosslinking agents for resols include hexamethylenetetramine and paraformaldehyde. The temperature and heating time required for heat curing and the amounts of heat-activatable curing agents can readily be determined in a known manner by preliminary tests.

A particular use of the mixtures according to the invention, containing novel copolymerizable sulfonium salts, is in the form of a photosensitive recording material for the production of relief images or resist patterns with a photosensitive curable layer applied to a dimensionally stable substrate.

We have found that the sulfonium salts used in novel mixtures are very suitable as heat-activatable and photochemically activatable catalysts for the photochemical elimination of phenolic protective groups and hence for solubility differentiation. Regarding further information on this use of the novel mixtures for such recording materials, reference may be made to DE-A-33 26 036, DE-A-32 31 147 and DE-A-32 31 145. The use of novel sulfonium salts of the formula (I) imparts to such recording materials a long shelf life coupled with a short post-curing time and in particular a uniform distribution of the initiator in the layer. For example, they can be stored for several weeks at 50° C. without any deterioration in the very good properties of the recording materials and in the high quality of the relief images or resist patterns produced therefrom.

Novel photosensitive recording materials are suitable for the production of letterpress, gravure, offset or screen printing plates, photoresists and soldering masks. They are also useful for laminating materials in the production of circuit boards, printed circuits, integrated circuits, etc. The production of relief images or resist patterns by means of the novel recording materials containing sulfonium salts can be carried out alternatively by the negative-working or positive-working method, as known per se and described in, for example, DE-A 23 09 062, DE-A 32 31 144, DE-A 32 31 145 and DE-A 32 31 147.

For all the compounds stated in the Examples below, the structure was confirmed by correct $^1$H-NMR, IR and mass spectra and by conforming elemental analyses.

In the Examples, percentages are by weight.

EXAMPLE 1

4-(N-(Methacryloylethyl)-carbamoyl)-phenyldimethylsulfonium hexafluoroarsenate 42.5 g of isocyanatoethyl methacrylate were added dropwise to a solution of 86 g of 4-hydroxyphenyldimethylsulfonium hexafluoroarsenate in 870 g of toluene and 443 g of tetrahydrofuran at room temperature. A solution of 3 g of triethylamine in 89 g of tetrahydrofuran was then added in the course of 10 minutes at an internal temperature of from 23° to 26° C., and the reaction mixture was stirred overnight at room temperature. The precipitated crystals were filtered off under suction, washed with toluene and recrystallized from ethanol. Yield: 110 g (88%) of colorless crystals of melting point 95°-97° C.

EXAMPLE 2

4-(N-(Methacryloylethyl)-carbamoyl)-phenyldimethylsulfonium hexafluorophosphate

A solution of 3 g of triethylamine in 89 g of tetrahydrofuran was added dropwise to a mixture of 870 g of toluene, 443 g of tetrahydrofuran, 90 g of 4-hydroxyphenyldimethylsulfonium hexafluorophosphate and 51 g of isocyanatoethyl methacrylate at from 20 to 25° C. in the course of 10 minutes, at a rate such that there was no marked temperature increase After 12 hours, the product was filtered off under suction, washed with toluene and recrystallized from ethanol. Yield: 112 g (82%) of colorless crystals of melting point 102°-104° C.

EXAMPLES 3 to 8

The following sulfonium salts were prepared by a method similar to those stated in Examples 1 and 2:

| Example No. | Compound | Anion | Yield [%] |
|---|---|---|---|
| 3 | {CH2=C(CH3)C(O)O-CH2CH2-NH-C(O)O-C6H4-}3 S⊕ | AsF6⊖ | 89 |
| 4 | {CH2=C(CH3)C(O)O-CH2CH2-NH-C(O)O-C6H4-}3 S⊕ | SbF6⊖ | 62 |
| 5 | {CH2=C(CH3)C(O)O-CH2CH2-NH-C(O)O-C6H4-}3 S⊕ | PF6⊖ | 77 |
| 6 | CH2=C(CH3)C(O)O-CH2CH2-O-CH2CH2-NH-C(O)O-C6H4-S⊕(CH3)2 | AsF6⊖ | 84 |
| 7 | CH2=C(CH3)C(O)O-CH2CH2-O-CH2CH2-NH-C(O)O-C6H4-S⊕(CH3)2 | PF6⊖ | 80 |
| 8 | [bis(methacryloyloxyethylcarbamato)phenyl]methyl(phenyl)sulfonium | PF6⊖ | 73 |

EXAMPLE 9

4-(1-Methacryloylethylcarbonato)-naphthyl)-tetrahydrothiophenium chloride

A mixture of 533 g of 4-(1-hydroxynaphthyl)tetrahydrothiophenium chloride and 540 g of hexamethyldisilazane was boiled for 8 hours at 100° C. in the absence of moisture. The mixture was cooled to room temperature, after which excess silazane was distilled off under reduced pressure from an oil pump and the residue (680 g) was dissolved in 2,300 g of acetonitrile. After the addition of 385 g of 2-chloroformylethyl methacrylate, heating was carried out for 5 hours at room temperature and for 5 hours under reflux. Chromatographic separation (silica gel/toluene) gave 4.8 g (57%) of a yellowish oil, which was pure according to $^1$H-NMR and $^{13}$C-NMR spectroscopy.

EXAMPLES 10 TO 17 (including Comparative Examples)

Surface coatings

The salts below were added as catalysts to 15% strength solutions of bisphenol A diglycidyl ether in acetone, in amounts such that the proportion of catalyst in each case was 3%, based on the bisphenol A diglycidyl ether.

The photosensitive mixtures prepared without heating were applied to glass sheets using an 80 μm knife coater (effective film thickness about 50 μm), dried in the air for 5 minutes to remove the acetone before exposure and conveyed past two lamps of 80 W/cm power in the air at a distance of about 10 cm at the belt speed stated in each case. The exposed films were evaluated immediately after exposure, after 2 hours and after 1 day, in accordance with the following quality characteristics:

| | |
|---|---|
| Gelled: | No longer free-flowing, tacky |
| Solid: | Surface non-tacky but without fingernail hardness |
| Completely cured: | Non-tacky, possesses fingernail hardness. |

TABLE 1
Curing of the surface coating

| Example No. | Compound | Immediately | Curing result Belt speed 3 m/min After 2 hours | After 1 day |
|---|---|---|---|---|
| 10* | 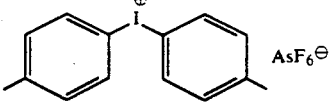 | Completely cured | Completely cured | Completely cured |
| 11* | 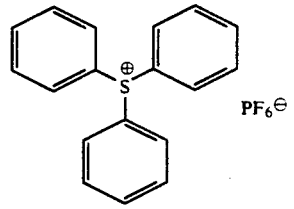 | Solid | Completely cured | Completely cured |
| 12 | 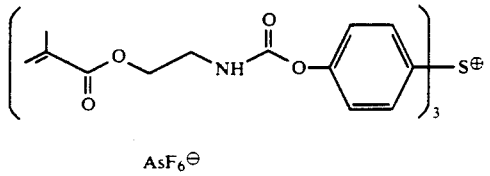 | Completely cured | Completely cured | Completely cured |
| 13 | 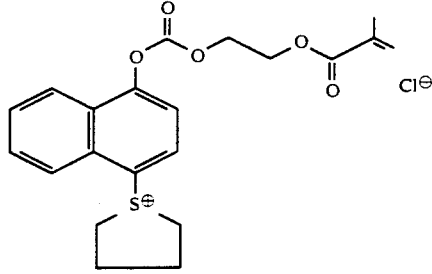 | Completely cured | Completely cured | Completely cured |

*Comparative Examples

TABLE 2
Curing of the surface coating

| Example No. | Compound | Immediately | Curing result Belt speed 15 m/min After 2 hours | After 1 day |
|---|---|---|---|---|
| 14* | 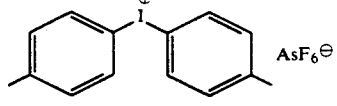 | Solid | Solid | Completely cured |
| 15* | 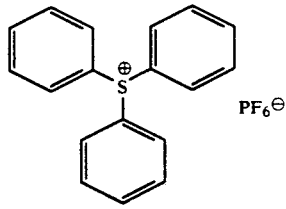 | Gelled | Solid | Solid |
| 16 | 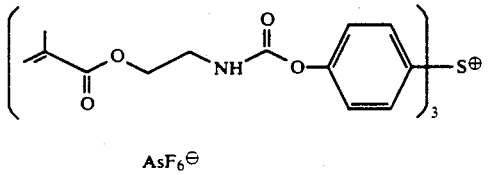 | Solid | Solid | Completely cured |

TABLE 2-continued

Curing of the surface coating

| Example No. | Compound | Immediately | Curing result Belt speed 15 m/min After 2 hours | After 1 day |
|---|---|---|---|---|
| 17 | 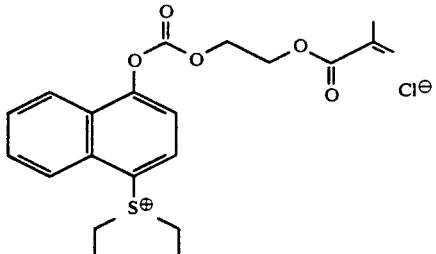 | Solid | Solid | Completely cured |

*Comparative Examples

As shown by the results stated in Tables 1 and 2, the novel mixtures of Examples 12, 13, 16 and 17 are as good as or better than those of the Comparative Examples, which, in Examples 10 and 14, contain a toxic catalyst salt.

With the aid of ESCA measurements, it is possible to show that the triarylsulfonium hexafluorophosphate (Comparative Examples 11 and 15) has, in the film, a concentration gradient which increases toward the substrate and is responsible for the poorer curing.

We claim:

1. A radiation-sensitive, ethylenically unsaturated, copolymerizable, organic compound of the formula (I)

$$[(R)_a(R^1)_b(R^2)_c S^{\oplus}] A^{\ominus} \quad (I)$$

where

R is an unsubstituted or substituted monovalent aromatic organic radical, $R^1$ is an unsubstituted or substituted monovalent organic aliphatic radical from the group consisting of the alkyl, cycloalkyl and substituted alkyl radicals, $R^2$ is an unsubstituted or substituted divalent or trivalent aliphatic or aromatic organic radical which forms a heterocylic or fused ring structure, a is an integer from 0 up to and including 3, b is an integer from 0 up to and including 2, c is the integer 0 or 1, the sum a+b+c being 3, $A^{\ominus}$ is an anion of an acid and at least one of the radicals R to $R^2$ contains one of the radicals

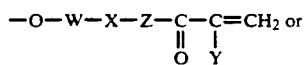

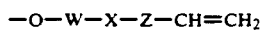

where

W is a single bond or one of the groups

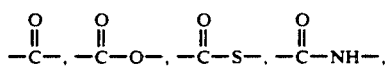

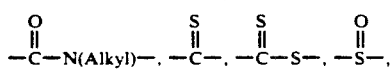

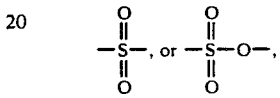

and

X is a divalent, unsubstituted or substituted alkylene radical —$(CH_2)_m$—, a radical

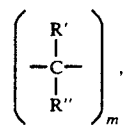

where m is from 1 to 10 and R' and R" are identical or different and are each aryl, $C_1$-$C_4$-alkyl, H, COOH, $COOCH_3$ or $COOC_2H_5$, or X is a perfluorinated alkylene radical —$(CF_2)_m$—, where m is from 1 to 10, an oxaalkylene radical —$(CH_2)_n$—O—$(CH_2)_p$—, where n and p are each from 1 to 5, a perfluorinated oxaalkylene radical —$(CF_2)_n$—O—$(CF_2)_p$—, where n and p are each from 1 to 5, or a polyoxaalkylene radical which may be perfluorinated and has from 2 to 20 oxygen atoms which are bonded to one another by at least one —$CH_2$—, —$CF_2$— or —$CH_2$—$CH(CH_3)$— group, or radical —$(CH_2)_m$—O—CO—O—$(CH_2)_n$—, —$(CH_2)_n$—O—CO—NH—$(CH_2)_m$—, —$(CH_2)_n$—NH—CO—O—$(CH_2)_m$—, —$(CH_2)_m$—CO—O—$(CH_2)_n$— or —$(CH_2)_m$—O—CO—$(CH_2)_n$—, where m and n are each from 1 to 10, a phenylene radical which is unsubstituted or substituted by alkyl of 1 to 4 carbon atoms, OH, $OCH_3$, $OC_2H_5$, SH, $SC_3$, $SC_2H_5$, F, N(alkyl)$_2$ or $N(CH_3)C_6H_5$ in the o-, m- or p-position, or a cycloalkylene radical of 5 to 10 carbon atoms, or a (bis)methylenecycloalkylene radical of 6 to 12 carbon atoms, Y is H, alkyl of 1 to 6 carbon atoms or phenyl and Z is O or NY.

2. A radiation sensitive composition which contains, as the photoinitiator, from 0.1 to 15% by weight of at least one ethylenically unsaturated, copolymerizable, radiation sensitive organic compound as claimed in claim 1, and one or more ethylenically unsaturated compounds copolymerizable therewith.

3. The composition of claim 2, which further includes a sensitiser or other conventional additives.

* * * * *

UNITED STATES PATENT AND TRADEMARK OFFICE
CERTIFICATE OF CORRECTION

PATENT NO. : 5,101,053

DATED : March 31, 1992

INVENTOR(S) : Andreas BOETTCHER

It is certified that error appears in the above-identified patent and that said Letters Patent is hereby corrected as shown below:

<u>Claim 1, Col. 24, Line 54</u>

Please insert --Cl-- between $SC_2H_5$, and F.

Signed and Sealed this

Tenth Day of August, 1993

Attest:

MICHAEL K. KIRK

Attesting Officer     Acting Commissioner of Patents and Trademarks